United States Patent [19]

Hofer et al.

[11] 4,097,592
[45] Jun. 27, 1978

[54] O-[1-SUBSTITUTED-6-PYRIDAZINON(3)YL]-THIONOALKANEPHOSPHONIC ACID ESTERS FOR COMBATING INSECTS AND ACARIDS

[75] Inventors: Wolfgang Hofer; Fritz Maurer; Hans-Jochem Riebel; Lothar Rohe; Rolf Schröder, all of Wuppertal; Ingeborg Hammann, Cologne; Wolfgang Behrenz, Overath-Steinenbrueck; Bernhard Homeyer, Leverkusen, all of Germany

[73] Assignee: Bayer Aktiengesellschaft, Leverkusen, Germany

[21] Appl. No.: 708,669

[22] Filed: Jul. 26, 1976

[30] Foreign Application Priority Data

Aug. 5, 1975 Germany .............................. 2534893

[51] Int. Cl.² .......................... C07F 9/65; A01N 9/36
[52] U.S. Cl. .................................. 424/200; 544/114; 544/232; 544/240
[58] Field of Search .................. 260/250 AP; 424/200

[56] References Cited

U.S. PATENT DOCUMENTS

| 2,759,937 | 8/1956 | Du Brevil | 260/250 AP |
|---|---|---|---|
| 3,310,560 | 3/1967 | Schoenbech et al. | 260/250 AP |
| 3,498,288 | 3/1976 | Hofer et al. | 260/250 AP |
| 3,544,572 | 11/1976 | Fest et al. | 260/250 AP |
| 3,749,720 | 7/1973 | Fest et al. | 260/250 AP |
| 3,867,397 | 2/1975 | Bohner et al. | 424/200 |
| 3,878,210 | 4/1975 | Lorenz et al. | 260/250 AP |
| 3,891,642 | 6/1975 | Lorenz et al. | 260/250 AP |
| 4,013,657 | 3/1977 | Hofer et al. | 260/250 AP |

FOREIGN PATENT DOCUMENTS

| 141,951 | 7/1971 | Czechoslovakia | 260/250 AP |
|---|---|---|---|
| 47/20025 | 7/1972 | Japan | 260/250 AP |

OTHER PUBLICATIONS

Shoenbech et al. II, Chem Abs. 67, 11497b(1967).
Fest et al III, Chem. Abs. 72, 100734y(1968).

*Primary Examiner*—Donald G. Daus
*Assistant Examiner*—Mark L. Berch
*Attorney, Agent, or Firm*—Burgess, Dinklage & Sprung

[57] ABSTRACT

O-[1-substituted-6-pyridazinon(3)yl]-thionoalkanephosphonic acid esters of the formula

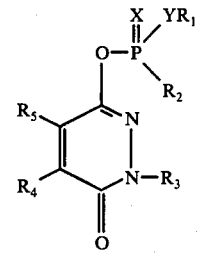

in which
R₁ and R₂ each independently is alkyl with 1 to 7 carbon atoms,
R₃ is alkyl, cyanoalkyl, alkylcarbonylalkyl, carbalkoxyalkyl, hydroxyalkyl, alkylthioalkyl or halogenalkyl with 1 to 4 carbon atoms per alkyl radical, alkenyl or alkynyl with 3 to 5 carbon atoms, benzyl, benzyl carrying at least one substituent selected from halogen and alkyl with 1 to 3 carbon atoms, phenyl, phenyl carrying at least one substituent selected from nitro, halogen, alkyl with 1 to 3 carbon atoms and carbalkoxy with 1 to 4 carbon atoms, morpholinomethyl or piperidinomethyl,
R₄ and R₅ each independently is hydrogen or alkyl with 1 to 3 carbon atoms, and
X and Y each independently is oxygen or sulfur,
which possess insecticidal and acaricidal properties.

10 Claims, No Drawings

O-[1-SUBSTITUTED-6-PYRIDAZINON(3)YL]-THIONOALKANEPHOSPHONIC ACID ESTERS FOR COMBATING INSECTS AND ACARIDS

The present invention relates to and has for its objects the provision of particular new O-[1-substituted-6-pyridazinon(3)yl]-thionoalkanephosphonic acid esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,759,937 and 3,310,560 and Netherlands Published Patent Application 6,904,664 that (thiono)pyridazinephosphoric(phosphonic) acid esters, for example O,O-diethyl-O-[1,6-dihydro-1-phenyl-(Compound A), -1-methyl-(Compound B), -1-carbethoxymethyl-(Compound C), -1-(2'-cyanoethyl)-(Compound D) and -1-(2'-methylcarbonylethyl)-6-pyridazinon(3)yl]-thionophosphoric acid esters (Compound E), O,O-diethyl-O-[1,6-dihydro-1-phenyl-6-pyridazinon(3)yl]-phosphoric acid ester (Compound F) and O-ethyl-O-[1,6-dihydro-6-pyridazinon(3)yl]-thionoethanephosphonic acid ester (Compound G), possess insecticidal and acaricidal properties.

The present invention provides, as new compounds, the (thiono)(thiol)-pyridazinone-alkanephosphonic acid esters of the general formula

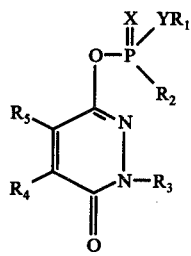

in which
$R_1$ and $R_2$ each independently is alkyl with 1 to 7 carbon atoms,
$R_3$ is alkyl, cyanoalkyl, alkylcarbonylalkyl, carbalkoxyalkyl, hydroxyalkyl, alkylthioalkyl or halogenalkyl with 1 to 4 carbon atoms per alkyl radical, alkenyl or alkynyl with 3 to 5 carbon atoms, benzyl, benzyl carrying at least one substituent selected from halogen and alkyl with 1 to 3 carbon atoms, phenyl, phenyl carrying at least one substituent selected from nitro, halogen, alkyl with 1 to 3 carbon atoms and carbalkoxy with 1 to 4 carbon atoms, morpholinomethyl or piperidinomethyl,
$R_4$ and $R_5$ each independently is hydrogen or alkyl with 1 to 3 carbon atoms, and
X and Y each independently is oxygen or sulfur.

Preferably, X represents sulfur, Y represents oxygen, $R_1$ represents straight-chain or branched alkyl with 1 to 5 carbon atoms, $R_2$ represents straight-chain or branched alkyl with 1 to 3 carbon atoms, $R_4$ and $R_5$ each represent hydrogen or methyl, and $R_3$ represents straight-chain or branched alkenyl or alkynyl with 3 or 4 carbon atoms, straight-chain or branched hydroxyalkyl, cyanoalkyl, alkylthioalkyl, chloroalkyl, methylcarbonylalkyl, ethylcarbonylalkyl, carbalkoxyalkyl or alkyl, each with 1 to 3 carbon atoms per alkyl radical, benzyl, chlorobenzyl, methylbenzyl, phenyl, phenyl substituted by nitro, chlorine, methyl, ethyl or carbalkoxy with 1 to 3 carbon atoms in the alkoxy radical, morpholinomethyl or piperidinomethyl.

Surprisingly, the (thiono)(thiol)pyridazinone-alkanephosphonic acid esters according to the invention exhibit a better insecticidal and acaricidal action than the corresponding previously known (thiono)pyridazinephosphoric(phosphonic) acid esters of analogous structure and of the same type of action. The products according to the present invention therefore represent a genuine enrichment of the art.

The present invention also provides a process for the preparation of a (thiono)(thiol)pyridazinone-alkanephosphonic acid ester of the formula (I), in which (a) a (thiono)(thiol)alkanephosphonic acid ester halide of the general formula

is reacted with a 3-hydroxy-6-pyridazinone derivative of the general formula

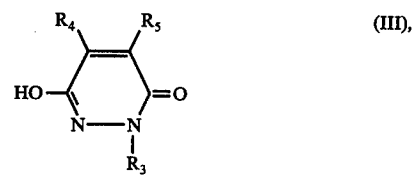

in which formulas
$R_1$ to $R_5$, X and Y have the above-mentioned meanings and
Hal represents halogen, preferably chlorine, if appropriate in the presence of a solvent and, if appropriate, in the presence of an acid acceptor, or (b), provided that a compound of the formula (I), in which $R_3$ represents alkenyl, alkynyl, cyanomethyl or carbalkoxymethyl is required, an O-[1,6-dihydro-6-pyridazon-(3)yl]-(thiono)(thiol)-alkanephosphonic acid ester of the general formula

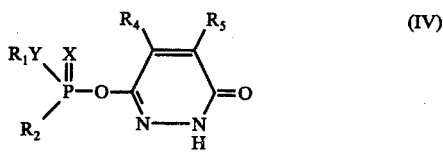

is reacted with a halide of the general formula

in which formulas $R_1$, $R_2$, $R_4$, $R_5$, X and Y have the above-mentioned meanings, Hal$_1$ represents halogen, preferably chlorine or bromine, and R$_6$ represents alkenyl or alkynyl with 3 to 6, preferably 3 or 4, carbon atoms, cyanomethyl or carbalkoxymethyl with 1 to 4, especially 1 to 3, carbon atoms in the alkoxy radical, if appropriate in the presence of a solvent and, if appropriate, in the presence of an acid acceptor, or (c), provided that a compound of the formula (I) in which R$_3$ represents hydroxymethyl is required, a compound of the formula (IV) above is reacted with formaldehyde of the formula

HCHO    (VI)

or (d), provided that a compound of the formula (I) in which R$_3$ represents chloromethyl is required, a compound of the formula (IV) above is reacted, in a first stage, with formaldehyde and the 1-hydroxymethyl compound so formed is reacted, without intermediate isolation of that reaction product, with thionyl chloride of the formula SOCl$_2$    (VII).

If, for example, S-isopropyl-thiolethanephosphonic acid chloride and 1,6-dihydro-1-(2'-hydroxyethyl)-3-hydroxy-6-pyridazinone, or O-ethyl-O-[1,6-dihydro-6-pyridazinon(3)-yl]-ethanephosphonic acid ester and allyl bromide or formaldehyde or formaldehyde and thionyl chloride are used as the starting materials, the course of the reactions can be represented by the following equations:

(a) 

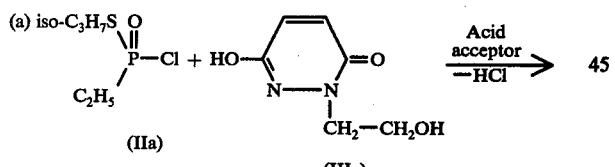

(b) 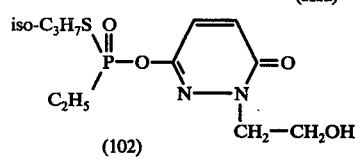

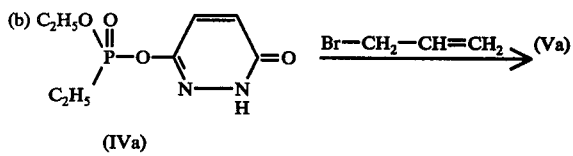

(c) 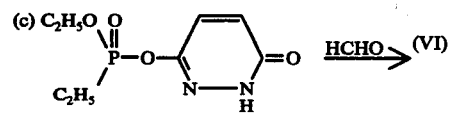

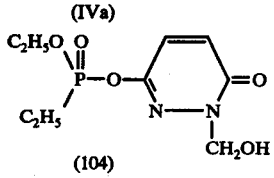

(d) 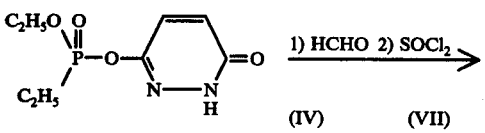

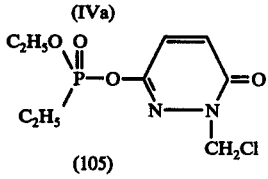

The (thiono)(thiol)alkanephosphonic acid ester halides (II) to be used as starting materials are known and are accessible in accordance with customary methods, for example, U.S. Pat. No. 3,167,574 and Belgian Patent No. 671,913, as are the halides (V), formaldehyde (VI) and thionyl chloride (VII), which can also be produced on a large industrial scale.

The following may be mentioned as examples: O-methyl-, O-ethyl-, O-n-propyl-, O-isopropyl-, O-n-butyl-, O-isobutyl-, O-tert.-butyl-, O-pentyl- and O-(2-methylbutyl)-methane-, ethane-, n-propane- and isopropane-phosphonic acid ester halides and the corresponding thiono analogues; S-methyl-, S-ethyl-, S-n-propyl-, S-isopropyl-, S-n-butyl-, S-isobutyl-, S-tert.-butyl-, and S-pentyl-methane-, ethane-, n-propane- and isopropane-thiolphosphonic acid ester halides and the corresponding thiono analogues; and cyanomethyl, carbo-methoxymethyl, carbethoxymethyl, carbo-n-propoxymethyl, carbo-isopropoxymethyl, allyl, propargyl and but-2-enyl chlorides and bromides.

3-Hydroxy-6-pyridazinone derivatives (III) to be used as starting materials have heretofore been described in the literature; they can be prepared in accordance with customary methods, for example from substituted hydrazines and maleic anhydrides or from maleic acid hydrazide and vinyl compounds, for example, J. Druey, Helv. 37, 510 (1954); K. Eichenberger, H. Staehelin and J. Druey, Helv. 37, 837 (1954); J. Feuer and R. Harmetz, J. Amer. Chem. Soc. 80, 5877 (1958), in accordance with the following equation:

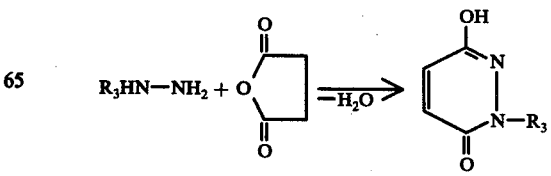

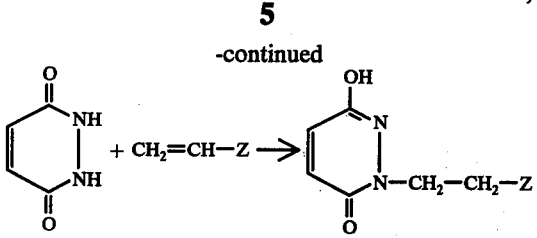

wherein
Z represents cyano, or alkylcarbonyl or carbalkoxy, each with 1 to 4 carbon atoms in the alkyl radical.

The following may be mentioned as examples of the 3-hydroxy-6-pyridazinone derivatives (III): 1-allyl-, 1-propargyl-, 1-but-2-enyl-, 1-cyanomethyl, 1-(2'-cyanoethyl)-, 1-(3'-cyanopropyl)-, 1-methylthiomethyl-, 1-ethylthiomethyl-, 1-n-propylthiomethyl-, 1-(2'-methylthioethyl)-, 1-(2'-ethylthioethyl)-, 1-(2'-n-propylthioethyl)-, 1-(3-ethylthiopropyl)-, 1-chloromethyl-, 1-(2'-chloroethyl)-, 1-(3'-chloropropyl)-, 1-hydroxymethyl-, 1-(2'-hydroxyethyl)-, 1-(3'-hydroxypropyl)-, 1-methyl-, 1-ethyl-, 1-n-propyl-, 1-isopropyl-, 1-methylcarbonylmethyl-, 1-ethylcarbonylmethyl-, 1-(2'-methylcarbonylethyl)-, 1-(2'-ethylcarbonylethyl)-, 1-(3'-methylcarbonylpropyl)-, 1-(3'-ethylcarbonylpropyl)-, 1-carbomethoxymethyl-, 1-carboethoxymethyl-, 1-carbo-n-propoxymethyl-, 1-(2'-carbomethoxyethyl)-, 1-(2'-carbethoxyethyl)-, 1(2'-carbo-n-propoxyethyl)-, 1-(3'-carbomethoxypropyl)-, 1-(3'-carbethoxypropyl)-, 1-(3'-carbo-n-propoxypropyl)-, 1-benzyl-, 1-(2'-chlorobenzyl)-, 1-(3'chlorobenzyl)-, 1-(4'-chlorobenzyl)-, 1-(2'-methylbenzyl)-, 1-(3'-methylbenzyl)-, 1-(4'-methylbenzyl)-, 1-(2'-ethylbenzyl)-, 1-(3'-ethylbenzyl)-, 1(4'-ethylbenzyl)-, 1-phenyl-, 1-(2'-chlorophenyl)-, 1(3'-chlorophenyl)-, 1-(4'-chlorophenyl)-, 1-(4',5'-dichlorophenyl)-, 1-(2'-nitrophenyl)-, 1-(3'-nitrophenyl)-, 1-(4'-nitrophenyl)-, 1-(3'carbomethoxyphenyl)-, 1-(3'-carbethoxyphenyl)-, 1-(3'-carbo-n-propoxyphenyl)-, 1-(4'-carbomethoxyphenyl)-, 1-(4'-carbethoxyphenyl)-, 1-(4'-carbo-n-propoxyphenyl)-, 1-(4'-carb-iso-propoxyphenyl)-, 1-(2'-methylphenyl)-, 1-(3'-methylphenyl)-, 1-(4'-methylphenyl)-, 1-(2'-ethylphenyl)-, 1(3'-ethylphenyl)-, 1-(4'-ethylphenyl)-, 1-morpholinomethyl- and 1-piperidinomethyl-1,6-dihydro-3-hydroxy-6-pyridazinones and the corresponding derivatives which are substituted by methyl in the 4- and/or 5-position.

The O-alkyl-O-[1,6-dihydro-6-pyridazinon(3)yl]-(thiono)-alkanephosphonic acid esters also to be used as starting materials are known from the literature, for example, Netherlands Published Patent Application No. 6,904,664, while the corresponding thiol compounds can be prepared in accordance with customary methods, by reacting the thiol(thiono)-alkanephosphonic acid ester halides with the corresponding 3-hydroxy-6-pyridazinone derivatives.

The following may be mentioned as specific examples: O-methyl-, O-ethyl-, O-n-propyl-, O-isopropyl-, O-n-butyl-, O-isobutyl-, O-sec.-butyl- or O-pentyl-O-[1,6-dihydro-6-pyridazinon(3)yl]-methane, ethane-, n-propane- and iso-propane-phosphonic acid esters and also S-methyl-, S-ethyl-, S-n-propyl-, S-isopropyl-, S-n-butyl-, S-sec.-butyl-, S-iso-butyl-, S-pentyl-O-[1,6-dihydro-6-pyridazinon(3)yl]-thiol-methan-, ethane-, n-propane- and iso-propane-phosphonic acid esters, and, in each case, the corresponding thiono analogues and/or the pyridazine derivatives which are methyl-substituted in the 4- or 5-position.

Process variants (a) and (b) and the 2nd stage of variant (d) are preferably carried out in the presence of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate and potassium carbonate, sodium methylate and ethylate, and potassium methylate, ethylate and tert.-butylate, have provided particularly successful, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 130° C, preferably at from 40° to 100° C.

Usually, the reaction is allowed to take place under normal pressure.

To carry out the process, the reactants are in general preferably employed in equimolar amounts. An excess of one or other component produces no significant advantages. Only in process variant (c) and in the first stage of process variant (d) is the formalin added in excess. In general, the reaction, in process variants (a), (b) and (c), is carried out by mixing the reactants, if appropriate in one of the solvents mentioned and, if appropriate, in the presence of an acid acceptor, filtering the solution, if necessary, after completion of the reaction, and pouring the solution into an organic solvent, for example toluene or methylene chloride. The organic phase is worked up in the usual manner by washing, drying and distilling off the solvent. Usually, in process variant (d), a mixture of excess formalin with the phosphoric acid component (IV) is heated and after conclusion of the reaction the batch is cooled and poured into an organic solvent, for example carbon tetrachloride, and thionyl chloride is added. Thereafter, the organic phase is worked up as described above.

The compounds of the present invention are in most cases obtained in the form of oils which cannot be distilled without decomposition but are freed from the last volatile constituents by so-called "slight distillation", that is to say by prolonged heating under reduced pressure to moderately elevated temperatures, and are purified in this way. They are characterized by the refractive index. Some compounds are obtained in a crystalline form and are characterized by their melting points.

As already mentioned, the (thiono)(thiol)-pyridazinone-alkanephosphonic acid esters according to the invention are distinguished by an excellent insecticidal and acaricidal activity. They are active against plant pests, pests harmful to health and pests of stored products and, in the veterinary medicine field, against animal parasites (ectoparasites).

They combine a low phytotoxicity with a good action against both sucking and biting insects and against mites, and they also exhibit relatively low mammalian toxicity.

For this reason, the compounds according to the invention can be employed successfully as pesticides in plant protection and in the hygiene field and field of protection of stored products, and also in the veterinary medicine field.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry blackfly (*Myzus cerasi*); in addition scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera) such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. avarage particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance along, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1

| | (Plutella test) | |
|---|---|---|
| Active compound | Active compound concentration in % | Degree of destruction in % after 3 days |
| (known) (C) 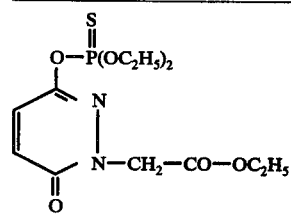 | 0.1<br>0.01<br>0.001 | 100<br>85<br>0 |
| (known) (E) 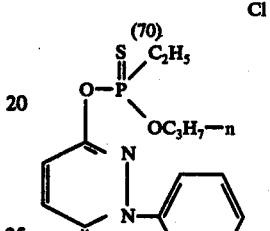 | 0.1<br>0.01<br>0.001 | 100<br>80<br>0 |
| (known) (D) 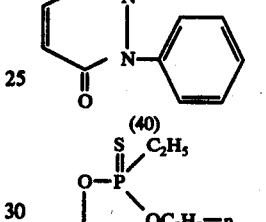 | 0.1<br>0.01<br>0.001 | 100<br>100<br>0 |
| (known) (A) 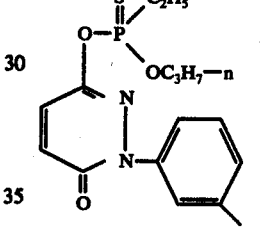 | 0.1<br>0.01<br>0.001 | 100<br>100<br>0 |
| (known) (F) 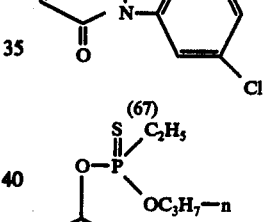 | 0.1<br>0.01<br>0.001 | 100<br>75<br>0 |
| (15) 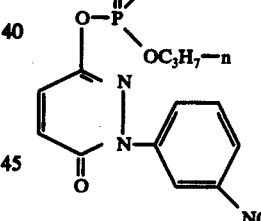 | 0.1<br>0.01<br>0.001 | 100<br>100<br>100 |

Table 1-continued

| | (Plutella test) | |
|---|---|---|
| Active compound | Active compound concentration in % | Degree of destruction in % after 3 days |
| 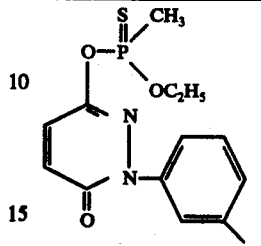 | 0.1<br>0.01<br>0.001 | 100<br>100<br>85 |
| (70) 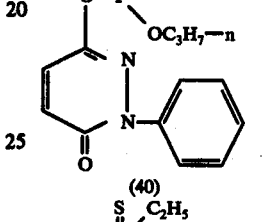 | 0.1<br>0.01<br>0.001 | 100<br>100<br>100 |
| (40) 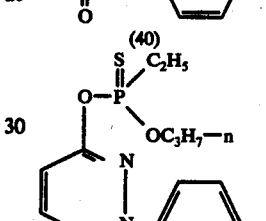 | 0.1<br>0.01<br>0.001 | 100<br>100<br>100 |
| (67) 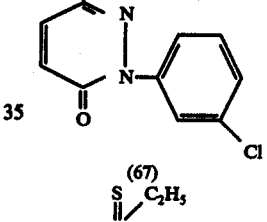 | 0.1<br>0.01<br>0.001 | 100<br>100<br>100 |
| (76) 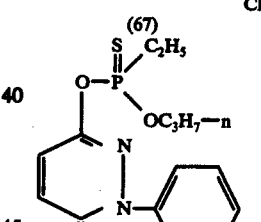 | 0.1<br>0.01<br>0.001 | 100<br>100<br>100 |
| (33) 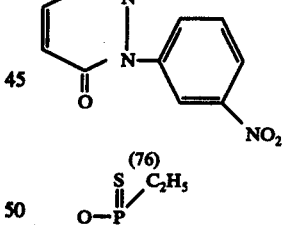 | 0.1<br>0.01<br>0.001 | 100<br>100<br>100 |
| (68) 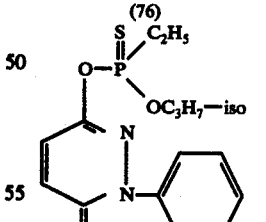 | | |

Table 1-continued
(Plutella test)

| Active compound | Active compound concentration in % | Degree of destruction in % after 3 days |
|---|---|---|
| Compound (20): O=P(O-)(OC₄H₉-iso)(OC₂H₅) on pyridazinone with N-phenyl | 0.1 / 0.01 / 0.001 | 100 / 100 / 100 |
| Compound (78): S=P(O-)(OC₄H₉-iso)(C₂H₅) on pyridazinone with N-CH₃ | 0.1 / 0.01 / 0.001 | 100 / 100 / 100 |

EXAMPLE 2

Laphygma test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all of the caterpillars had been killed whilst 0% indicates that no caterpillars had been killed.

The active compounds, the concentrations of the active compound, the evaluation times and the results can be seen from the following table:

Table 2
(Laphygma test)

| Active compound | Active compound concentration in % | Degree of destruction in % after 3 days |
|---|---|---|
| (known) (E): O=P(OC₂H₅)₂, S, on pyridazinone with N-CH₂-CH₂-CO-CH₃ | 0.1 / 0.01 | 100 / 0 |
| (14): S=P(O-)(OCH₃)(C₂H₅) on pyridazinone with N-CH₃ | 0.1 / 0.01 | 100 / 100 |
| (91): S=P(O-)(OC₃H₇-iso)(CH₃) on pyridazinone with N-CH₂-OH | 0.1 / 0.01 | 100 / 100 |
| (88): S=P(O-)(OC₃H₇-iso)(CH₃) on pyridazinone with N-CH₂-CH=CH₂ | 0.1 / 0.01 | 100 / 100 |
| (81): S=P(O-)(OC₂H₅)(C₂H₅) on pyridazinone with N-CH₂-CH=CH₂ | 0.1 / 0.01 | 100 / 100 |
| (56): S=P(O-)(OC₂H₅)(C₂H₅) on pyridazinone with N-CH₂-CH₂-Cl | 0.1 / 0.01 | 100 / 100 |
| (3): S=P(O-)(OC₂H₅)(C₂H₅) on pyridazinone with N-CH₂-CH₂-CN | 0.1 / 0.001 | 100 / 100 |

Table 2-continued
(Laphygma test)

| Active compound | Active compound concentration in % | Degree of destruction in % after 3 days |
|---|---|---|
| (28) | 0.1 / 0.01 | 100 / 100 |
| (29) | 0.1 / 0.01 | 100 / 100 |
| (73) | 0.1 / 0.01 | 100 / 100 |
| (71) | 0.1 / 0.01 | 100 / 100 |
| (74) | 0.1 / 0.01 | 100 / 100 |
| (64) | 0.1 / 0.01 | 100 / 100 |
| (65) | 0.1 / 0.01 | 100 / 100 |
| (51) | 0.1 / 0.01 | 100 / 100 |
| (75) | 0.1 / 0.01 | 100 / 100 |
| (42) | 0.1 / 0.01 | 100 / 100 |
| (80) | 0.1 / 0.01 | 100 / 100 |

EXAMPLE 3

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3
(*Myzus* test)

| Active compound | Active compound concentration in % | Degree of destruction in % after 1 day |
|---|---|---|
| (known) (G) | 0.1 / 0.01 / 0.001 | 100 / 99 / 0 |
| (known) (E) | 0.1 / 0.01 / 0.001 | 100 / 80 / 0 |
| (known) (A) | 0.1 / 0.01 / 0.001 | 100 / 98 / 0 |
| (known) (F) | 0.1 / 0.01 / 0.001 | 100 / 75 / 0 |
| (27) | 0.1 / 0.01 / 0.001 | 100 / 100 / 98 |
| (16) | 0.1 / 0.01 / 0.001 | 100 / 100 / 85 |
| (36) | 0.1 / 0.01 / 0.001 | 100 / 100 / 99 |
| (14) | 0.1 / 0.01 / 0.001 | 100 / 100 / 98 |
| (34) | 0.1 / 0.01 / 0.001 | 100 / 100 / 98 |
| (1) | 0.1 / 0.01 / 0.001 | 100 / 100 / 99 |
| (37) | 0.1 / 0.01 / 0.001 | 100 / 100 / 100 |
| (38) | 0.1 / 0.01 / 0.001 | 100 / 100 / 99 |

Table 3-continued
(Myzus test)

| Active compound | Active compound concentration in % | Degree of destruction in % after 1 day |
|---|---|---|
| 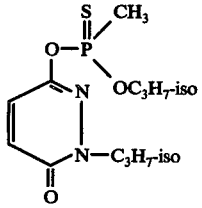 | 0.1<br>0.01<br>0.001 | 100<br>100<br>100 |
| (85)<br>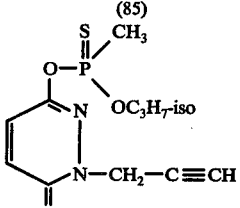 | 0.1<br>0.01<br>0.001 | 100<br>100<br>98 |
| (86)<br>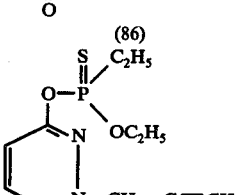 | 0.1<br>0.01<br>0.001 | 100<br>100<br>99 |
| (84)<br>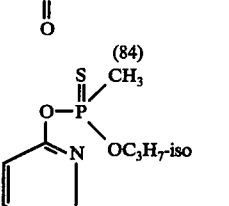 | 0.1<br>0.01<br>0.001 | 100<br>100<br>99 |
| (89)<br>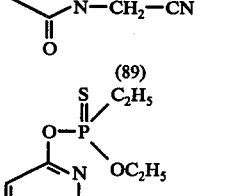 | 0.1<br>0.01<br>0.001 | 100<br>100<br>99 |
| (83)<br>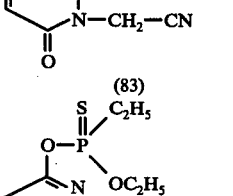 | 0.1<br>0.01<br>0.001 | 100<br>100<br>100 |
| (81)<br>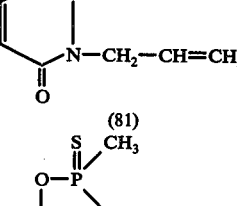 | 0.1<br>0.01<br>0.001 | 100<br>100<br>100 |
| (57)<br>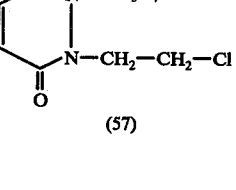 | 0.1<br>0.01<br>0.001 | 100<br>100<br>99 |
| (58)<br>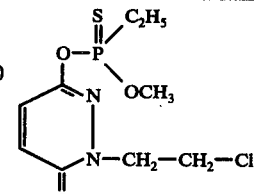 | 0.1<br>0.01<br>0.001 | 100<br>100<br>100 |
| (56)<br>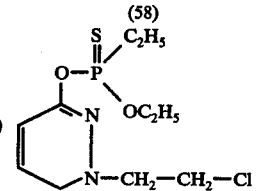 | 0.1<br>0.01<br>0.001 | 100<br>100<br>95 |
| (24)<br>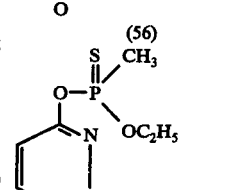 | 0.1<br>0.01<br>0.001 | 100<br>100<br>98 |
| (4)<br>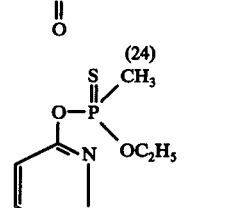 | 0.1<br>0.01<br>0.001 | 100<br>100<br>95 |
| (6)<br>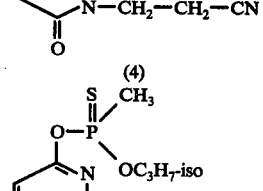 | 0.1<br>0.01<br>0.001 | 100<br>100<br>98 |
| (5)<br>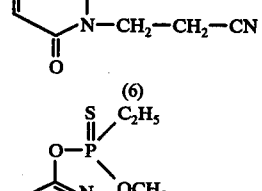 | 0.1<br>0.01<br>0.001 | 100<br>100<br>95 |
| (7) | | |

Table 3-continued
(Myzus test)

| Active compound | Active compound concentration in % | Degree of destruction in % after 1 day |
|---|---|---|
| Structure (87): O=P(S)(CH₃)(OC₃H₇-iso)–O–[pyridazinone ring]–N–CH₂–CO–OC₂H₅ | 0.1<br>0.01<br>0.001 | 100<br>100<br>95 |
| Structure (82): O=P(S)(C₂H₅)(OC₂H₅)–O–[pyridazinone]–N–CH₂–CO–OC₂H₅ | 0.1<br>0.01<br>0.001 | 100<br>100<br>70 |
| Structure (10): O=P(S)(CH₃)(OC₂H₅)–O–[pyridazinone]–N–CH₂–CH₂–CO–OCH₃ | 0.1<br>0.01<br>0.001 | 100<br>100<br>95 |
| Structure (12): O=P(S)(CH₃)(OC₂H₅)–O–[pyridazinone]–N–CH₂–CH₂–CO–OC₂H₅ | 0.1<br>0.01<br>0.001 | 100<br>100<br>99 |
| Structure (11): O=P(S)(C₂H₅)(OC₂H₅)–O–[pyridazinone]–N–CH₂–CH₂–CO–OCH₃ | 0.1<br>0.01<br>0.001 | 100<br>100<br>95 |
| Structure (9): O=P(S)(C₂H₅)(OC₃H₇-n)–O–[pyridazinone]–N–CH₂–CH₂–CO–OCH₃ | 0.1<br>0.01<br>0.001 | 100<br>100<br>90 |
| Structure (13): O=P(S)(C₂H₅)(OC₂H₅)–O–[pyridazinone]–N–CH₂–CH₂–CO–OC₂H₅ | 0.1<br>0.01<br>0.001 | 100<br>100<br>95 |
| Structure (70): O=P(S)(CH₃)(OC₂H₅)–O–[pyridazinone]–N–(3-Cl–C₆H₄) | 0.1<br>0.01<br>0.001 | 100<br>100<br>95 |
| Structure (69): O=P(S)(C₂H₅)(OCH₃)–O–[pyridazinone]–N–(3-Cl–C₆H₄) | 0.1<br>0.01<br>0.001 | 100<br>100<br>98 |
| Structure (67): O=P(S)(C₂H₅)(OC₃H₇-n)–O–[pyridazinone]–N–(3-Cl–C₆H₄) | 0.1<br>0.01<br>0.001 | 100<br>100<br>99 |
| Structure (68): O=P(S)(C₂H₅)(OC₃H₇-iso)–O–[pyridazinone]–N–(3-Cl–C₆H₄) | 0.1<br>0.01<br>0.001 | 100<br>100<br>98 |
| Structure (50): O=P(S)(C₂H₅)(OC₂H₅)–O–[pyridazinone]–N–(C₆H₄–CO–OC₂H₅) | 0.1<br>0.01<br>0.001 | 100<br>100<br>90 |
| Structure (44): O=P(S)(CH₃)(OC₃H₇-iso)–O–[pyridazinone]–N–(4-Cl–C₆H₄) | 0.1<br>0.01<br>0.001 | 100<br>100<br>99 |

Table 3-continued
(Myzus test)

| Active compound | Active compound concentration in % | Degree of destruction in % after 1 day |
|---|---|---|
| 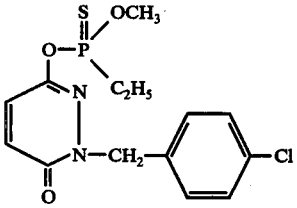 (45) | 0.1<br>0.01<br>0.001 | 100<br>100<br>99 |
| 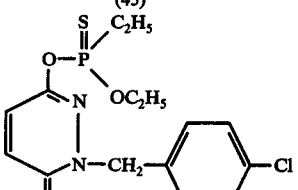 (43) | 0.1<br>0.01<br>0.001 | 100<br>100<br>100 |
| 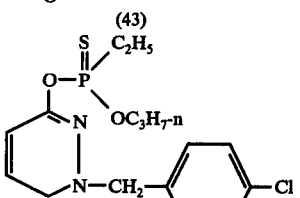 (46) | 0.1<br>0.01<br>0.001 | 100<br>100<br>85 |
| 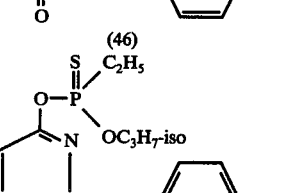 (49) | 0.1<br>0.01<br>0.001 | 100<br>100<br>100 |
| 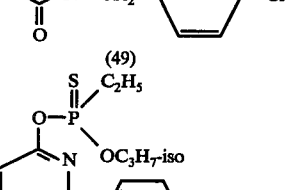 (66) | 0.1<br>0.01<br>0.001 | 100<br>100<br>99 |
| 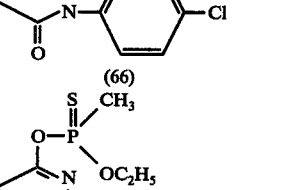 (41) | 0.1<br>0.01<br>0.001 | 100<br>100<br>100 |
| 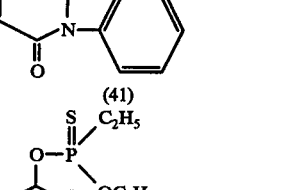 (31) | 0.1<br>0.01<br>0.001 | 100<br>100<br>100 |
| 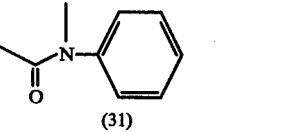 (40) | 0.1<br>0.01<br>0.001 | 100<br>100<br>99 |
| 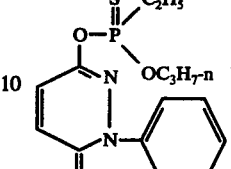 (32) | 0.1<br>0.01<br>0.001 | 100<br>100<br>85 |
| 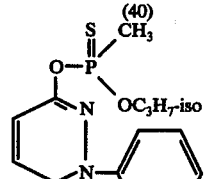 (48) | 0.1<br>0.01<br>0.001 | 100<br>100<br>98 |
| 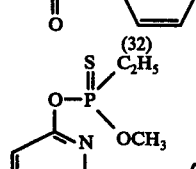 (47) | 0.1<br>0.01<br>0.001 | 100<br>100<br>95 |
| 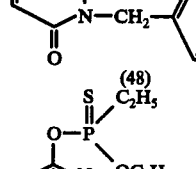 (78) | 0.1<br>0.01<br>0.001 | 100<br>100<br>99 |
| 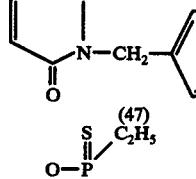 (80) | 0.1<br>0.01<br>0.001 | 100<br>100<br>70 |

EXAMPLE 4

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound so that this preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following table:

Table 4

(*Doralis* test/systemic action)

| Active compound | Active compound concentration in % | Degree of destruction in % after 4 days |
| --- | --- | --- |
| $\underset{\text{(known)\quad (C)}}{\text{structure: } O-P(OC_2H_5)_2 \text{ with } S\text{=}P, \text{ attached to ring with } N, N-CH_2-CO-OC_2H_5, O}$ | 0.1 | 0 |
| $\underset{\text{(known)\quad (A)}}{\text{structure: } O-P(OC_2H_5)_2 \text{ with } S\text{=}P, \text{ ring with } N-C_6H_5, O}$ | 0.1 | 0 |
| $\underset{(93)}{\text{structure: } O-P(CH_3)(OC_3H_7\text{-iso}), S\text{=}P, \text{ring, } N-CH_2-Cl}$ | 0.1<br>0.01 | 100<br>100 |
| $\underset{(3)}{\text{structure: } O-P(C_2H_5)(OC_2H_5), S\text{=}P, \text{ring, } N-CH_2-CH_2-CN}$ | 0.1<br>0.01 | 100<br>100 |
| $\underset{(23)}{\text{structure: } O-P(CH_3)(OC_3H_7\text{-iso}), S\text{=}P, \text{ring, } N-CH_2-N(\text{morpholine})}$ | 0.1<br>0.01 | 100<br>70 |

Table 4-continued (*Doralis* test/systemic action)

| Active compound | Active compound concentration in % | Degree of destruction in % after 4 days |
|---|---|---|
| Compound (22): Pyridazinone with $O-P(=S)(C_2H_5)(OC_2H_5)$ group and N-CH$_2$-morpholine substituent | 0.1<br>0.01 | 100<br>100 |
| Compound (80): Pyridazinone with $O-P(=S)(CH_3)(OC_4H_9\text{-sec.})$ group and N-CH$_3$ substituent | 0.1<br>0.01 | 100<br>100 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*) were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 5

(*Tetranychus* test)

| Active compound | Active compound concentration in % | Degree of destruction in % after 2 days |
|---|---|---|
| Pyridazinone with $O-P(=S)(C_2H_5)(OC_2H_5)$ group and NH (known) (G) | 0.1<br>0.01 | 95<br>0 |
| Pyridazinone with $O-P(=S)(OC_2H_5)_2$ group and N-CH$_2$-CH$_2$-CO-CH$_3$ substituent (known) (E) | 0.1<br>0.01 | 98<br>0 |

Table 5-continued

| Active compound | (*Tetranychus* test) Active compound concentration in % | Degree of destruction in % after 2 days |
| --- | --- | --- |
| (known) (F) [structure: O=P(OC₂H₅)₂–O–pyridazinone–N–phenyl] | 0.1<br>0.01 | 20<br>0 |
| (27a) (Isomer mixture) [structure with P(=S)(CH₃)(OC₂H₅), methylated pyridazinone, N–CH₃] | 0.1<br>0.01 | 100<br>95 |
| (15) [structure with P(=S)(CH₃)(OC₂H₅), pyridazinone, N–CH₃] | 0.1<br>0.01 | 99<br>98 |
| (16) [structure with P(=S)(CH₃)(OC₃H₇-iso), pyridazinone, N–CH₃] | 0.1<br>0.01 | 100<br>100 |
| (1) [structure with P(=S)(C₂H₅)(OC₂H₅), pyridazinone, N–CH₃] | 0.1<br>0.01 | 100<br>99 |
| (85) [structure with P(=S)(CH₃)(OC₃H₇-iso), pyridazinone, N–C₃H₇-iso] | 0.1<br>0.01 | 100<br>100 |

Table 5-continued
(*Tetranychus* test)

| Active compound | Active compound concentration in % | Degree of destruction in % after 2 days |
|---|---|---|
| Compound (88): O-P(=S)(CH₃)(OC₃H₇-iso) linked to pyridazinone with N–CH₂–CH=CH₂ | 0.1<br>0.01 | 100<br>100 |
| Compound (86): O-P(=S)(CH₃)(OC₃H₇-iso) linked to pyridazinone with N–CH₂–C≡CH | 0.1<br>0.01 | 100<br>100 |
| Compound (89): O-P(=S)(CH₃)(OC₃H₇-iso) linked to pyridazinone with N–CH₂–CN | 0.1<br>0.01 | 100<br>100 |
| Compound (83): O-P(=S)(C₂H₅)(OC₂H₅) linked to pyridazinone with N–CH₂–CN | 0.1<br>0.01 | 100<br>95 |
| Compound (87): O-P(=S)(CH₃)(OC₃H₇-iso) linked to pyridazinone with N–CH₂–CO–OC₂H₅ | 0.1<br>0.01 | 100<br>99 |
| Compound (57): O-P(=S)(CH₃)(OC₃H₇-iso) linked to pyridazinone with N–CH₂–CH₂–Cl | 0.1<br>0.01 | 100<br>98 |
| Compound (24): O-P(=S)(CH₃)(OC₂H₅) linked to pyridazinone with N–CH₂–CH₂–SC₂H₅ | 0.1<br>0.01 | 100<br>100 |

Table 5-continued

| Active compound | (Tetranychus test) Active compound concentration in % | Degree of destruction in % after 2 days |
|---|---|---|
| Compound (25): O-isopropyl O-(1-(2-ethylthioethyl)-6-oxo-1,6-dihydropyridazin-3-yl) methylphosphonothioate | 0.1<br>0.01 | 100<br>99 |
| Compound (26): O-ethyl O-(1-(2-ethylthioethyl)-6-oxo-1,6-dihydropyridazin-3-yl) ethylphosphonothioate | 0.1<br>0.01 | 100<br>98 |
| Compound (11): O-ethyl O-(1-(3-oxobutyl)-6-oxo-1,6-dihydropyridazin-3-yl) ethylphosphonothioate | 0.1<br>0.01 | 100<br>90 |
| Compound (10): O-ethyl O-(1-(2-methoxycarbonylethyl)-6-oxo-1,6-dihydropyridazin-3-yl) methylphosphonothioate | 0.1<br>0.01 | 100<br>70 |
| Compound (4): O-ethyl O-(1-(2-cyanoethyl)-6-oxo-1,6-dihydropyridazin-3-yl) methylphosphonothioate | 0.1<br>0.01 | 100<br>90 |
| Compound (6): O-isopropyl O-(1-(2-cyanoethyl)-6-oxo-1,6-dihydropyridazin-3-yl) methylphosphonothioate | 0.1<br>0.01 | 100<br>80 |
| Compound (3): O-ethyl O-(1-(2-cyanoethyl)-6-oxo-1,6-dihydropyridazin-3-yl) ethylphosphonothioate | 0.1<br>0.01 | 100<br>98 |

Table 5-continued

| Active compound | (Tetranychus test) Active compound concentration in % | Degree of destruction in % after 2 days |
|---|---|---|
| (39) | 0.1 / 0.01 | 100 / 100 |
| (41) | 0.1 / 0.01 | 100 / 100 |
| (32) | 0.1 / 0.01 | 100 / 100 |
| (30) | 0.1 / 0.01 | 100 / 98 |
| (28) | 0.1 / 0.01 | 100 / 100 |
| (40) | 0.1 / 0.01 | 100 / 80 |
| (77) | 0.1 / 0.01 | 100 / 90 |

Table 5-continued
(*Tetranychus* test)

| Active compound | Active compound concentration in % | Degree of destruction in % after 2 days |
|---|---|---|
| (42) | 0.1<br>0.01 | 100<br>100 |
| (65) | 0.1<br>0.01 | 100<br>99 |
| (44) | 0.1<br>0.01 | 100<br>100 |
| (66) | 0.1<br>0.01 | 100<br>100 |
| (70) | 0.1<br>0.01 | 100<br>100 |
| (69) | 0.1<br>0.01 | 100<br>80 |
| (21) | 0.1<br>0.01 | 98<br>90 |

EXAMPLE 6

Critical concentration test/soil insects
Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 6

Critical concentration test/soil insects
(*Tenebrio molitor* larvae in the soil)

| Active compound | Degree of destruction in % at an active compound concentration of 20 ppm |
|---|---|
| (known) (G) | 0 |
| (known) (F) | 0 |
| (known) (C) | 0 |
| (known) (B) | 0 |
| (known) (E) | 0 |
| (known) (D) | 0 |
| (37) | 100 |
| (85) | 100 |
| (42) | 100 |
| (49) | 100 |

Table 6-continued

Critical concentration test/soil insects
(*Tenebrio molitor* larvae in the soil)

| Active compound | Degree of destruction in % at an active compound concentration of 20 ppm |
|---|---|
| (88) structure with S=P(CH₃)(OC₃H₇-iso), N—CH₂—CH=CH₂ | 100 |
| (20) structure with S=P(C₂H₅)(O—C₄H₉-iso), N-phenyl | 100 |

EXAMPLE 7

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 7

Critical concentration test/soil insects
(*Phorbia antiqua* grubs in the soil)

| Active compound | | Degree of destruction in % at an active compound concentration of 20 ppm |
|---|---|---|
| (known) pyridazinone with S=P(C₂H₅)(OC₂H₅), N—H | (G) | 0 |
| (known) pyridazinone with O=P(OC₂H₅)₂, N-phenyl | (F) | 0 |
| (known) pyridazinone with S=P(OC₂H₅)₂, N—CH₂—CO—OC₂H₅ | (C) | 0 |
| (known) pyridazinone with S=P(OC₂H₅)₂, N—CH₃ | (B) | 0 |
| (known) pyridazinone with S=P(OC₂H₅)₂, N—CH₂—CH₂—CO—CH₃ | (E) | 0 |
| (known) pyridazinone with S=P(OC₂H₅)₂, N—CH₂—CH₂—CN | (D) | 0 |

Table 7-continued

Critical concentration test/soil insects
*(Phorbia antiqua grubs in the soil)*

| Active compound | | Degree of destruction in % at an active compound concentration of 20 ppm |
|---|---|---|
| Compound with P(=S)(CH₃)(OC₃H₇-iso), pyridazinone with 4-Cl-phenyl | (65) | 100 |
| Compound with P(=S)(C₂H₅)(OC₃H₇-iso), pyridazinone with 4-Cl-phenyl | (66) | 100 |
| Compound with P(=S)(C₂H₅)(OC₃H₇-n), pyridazinone with 3-Cl-phenyl | (67) | 100 |
| Compound with P(=S)(C₂H₅)(OC₃H₇-iso), pyridazinone with 3-Cl-phenyl | (68) | 100 |
| Compound with P(=S)(CH₃)(OC₃H₇-iso), pyridazinone with 4-CH₃-phenyl | (71) | 100 |
| Compound with P(=S)(C₂H₅)(OC₃H₇-iso), pyridazinone with 3-NO₂-phenyl | (75) | 100 |
| Compound with P(=S)(C₂H₅)(OC₃H₇-n), pyridazinone with 3-NO₂-phenyl | (76) | 100 |
| Compound with P(=S)(C₂H₅)(OC₂H₅), 5-CH₃ pyridazinone with phenyl | (29) | 100 |
| Compound with P(=S)(C₂H₅)(OC₂H₅), pyridazinone with phenyl | (31) | 100 |
| Compound with P(=S)(CH₃)(OC₃H₇-iso), pyridazinone with phenyl | (32) | 100 |
| Compound with P(=S)(C₂H₅)(OC₃H₇-iso), pyridazinone with phenyl | (33) | 100 |
| Compound with P(=S)(C₂H₅)(OC₂H₅), 5-CH₃, N-CH₃ pyridazinone | (37) | 100 |

Table 7-continued

Critical concentration test/soil insects
(*Phorbia antiqua* grubs in the soil)

| Active compound | | Degree of destruction in % at an active compound concentration of 20 ppm |
|---|---|---|
| [Structure: O-P(=S)(C₂H₅)(OC₃H₇-n) on pyridazinone with N-phenyl] | (40) | 100 |
| [Structure: O-P(=S)(CH₃)(OC₃H₇-iso) on pyridazinone with N-C₃H₇-iso] | (85) | 100 |
| [Structure: O-P(=S)(CH₃)(OC₃H₇-iso) on pyridazinone with N-CH₂-C₆H₄-CH₃] | (42) | 100 |
| [Structure: O-P(=S)(C₂H₅)(OC₂H₅) on pyridazinone with N-CH₂-C₆H₄-Cl] | (43) | 100 |
| [Structure: O-P(=S)(CH₃)(OC₃H₇-iso) on pyridazinone with N-CH₂-C₆H₄-Cl] | (44) | 100 |
| [Structure: O-P(=S)(OCH₃)(C₂H₅) on pyridazinone with N-CH₂-C₆H₄-Cl] | (45) | 100 |
| [Structure: O-P(=S)(C₂H₅)(OC₃H₇-n) on pyridazinone with N-CH₂-C₆H₄-Cl] | (46) | 100 |
| [Structure: O-P(=S)(C₂H₅)(OC₂H₅) on pyridazinone with N-CH₂-C₆H₄-CH₃] | (47) | 100 |
| [Structure: O-P(=S)(C₂H₅)(OCH₃) on pyridazinone with N-CH₂-C₆H₄-CH₃] | (48) | 100 |
| [Structure: O-P(=S)(C₂H₅)(OC₃H₇-iso) on pyridazinone with N-CH₂-C₆H₄-Cl] | (49) | 100 |
| [Structure: O-P(=S)(CH₃)(OC₃H₇-iso) on pyridazinone with N-CH₂-C≡CH] | (86) | 100 |
| [Structure: O-P(=S)(CH₃)(OC₃H₇-iso) on pyridazinone with N-CH₂-CO-OC₂H₅] | (87) | 100 |
| [Structure: O-P(=S)(C₂H₅)(OC₂H₅) on pyridazinone with N-C₆H₄-CO-OC₂H₅] | (50) | 100 |

Table 7-continued

Critical concentration test/soil insects
(*Phorbia antiqua* grubs in the soil)

| Active compound | | Degree of destruction in % at an active compound concentration of 20 ppm |
|---|---|---|
| [structure with OC₃H₇-iso, N-phenyl-CO-OC₂H₅] | (51) | 100 |
| [structure with OC₃H₇-iso, N-CH₂-CH=CH₂] | (88) | 100 |
| [structure with OC₃H₇-iso, N-CH₂-CN] | (89) | 100 |
| [structure with OC₂H₅, N-CH₂-CO-OC₂H₅] | (82) | 100 |
| [structure with OC₂H₅, N-CH₂-CN] | (83) | 100 |
| [structure with OC₂H₅, N-CH₃] | (1) | 100 |
| [structure with OC₃H₇-iso, N-CH₃] | (16) | 100 |
| [structure with OC₂H₅, N-CH₂-C≡CH] | (84) | 100 |
| [structure with OC₂H₅, N-CH₂-CH=CH₂] | (81) | 100 |
| [structure with O-C₄H₉-iso, N-phenyl] | (20) | 100 |
| [structure with SC₄H₉-sec., N-(p-tolyl)] | (60) | 100 |

EXAMPLE 8

LT₁₀₀ test for Diptera
Test insects: *Aëdes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 8

LT$_{100}$ test for Diptera (*Aëdes aegypti*)

| Active compound | Active compound concentration of the solution in % | LT$_{100}$ in minutes (') |
|---|---|---|
| (known) (G) | 0.2<br>0.02 | 180'<br>180' = 0% |
| (known) (F) | 0.2<br>0.02 | 120'<br>180' = 0% |
| (known) (E) | 0.2<br>0.02<br>0.002 | 120'<br>180' = 90%<br>180' = 0% |
| (known) (D) | 0.2<br>0.02<br>0.002 | 120'<br>180'<br>180' = 0% |

Table 8-continued

LT$_{100}$ test for Diptera (*Aëdes aegypti*)

| Active compound | Active compound concentration of the solution in % | LT$_{100}$ in minutes (') |
|---|---|---|
| (known) (C) | 0.2<br>0.02 | 120'<br>180' = 50% |
| (14) | 0.2<br>0.02 | 60'<br>60' |
| (15) | 0.2<br>0.02 | 60'<br>60' |
| (1) | 0.2<br>0.02 | 60'<br>60' |
| (16) | 0.2<br>0.02 | 60'<br>60' |
| (37) | 0.2<br>0.02 | 60'<br>120' |

Table 8-continued

LT$_{100}$ test for Diptera (Aëdes aegypti)

| Active compound | Active compound concentration of the solution in % | LT$_{100}$ in minutes (') |
|---|---|---|
| Compound (27): O=P(S)(CH$_3$)(OC$_2$H$_5$)–O–[pyridazinone with CH$_3$, N–CH$_3$] | 0.2<br>0.02 | 60'<br>120' |
| Compound (94): O=P(S)(OC$_3$H$_7$-n)(CH$_3$)–O–[pyridazinone, N–C$_3$H$_7$-n] | 0.2<br>0.02 | 60'<br>120' |
| Compound (81): O=P(S)(C$_2$H$_5$)(OC$_2$H$_5$)–O–[pyridazinone, N–CH$_2$–CH=CH$_2$] | 0.2<br>0.02 | 60'<br>120' |
| Compound (95): O=P(S)(OC$_3$H$_7$-n)(CH$_3$)–O–[pyridazinone, N–CH$_2$–CH=CH$_2$] | 0.2<br>0.02 | 60'<br>120' |
| Compound (76): O=P(S)(OC$_3$H$_7$-n)(CH$_3$)–O–[pyridazinone, N–CH$_2$–C≡CH] | 0.2<br>0.02 | 60'<br>120' |
| Compound (84): O=P(S)(C$_2$H$_5$)(OC$_2$H$_5$)–O–[pyridazinone, N–CH$_2$–C≡CH] | 0.2<br>0.02 | 60'<br>120' |
| Compound (97): O=P(S)(OC$_3$H$_7$-n)(CH$_3$)–O–[pyridazinone, N–CH$_2$–CH$_2$–Cl] | 0.2<br>0.02 | 60'<br>120' |

EXAMPLE 9

LD$_{100}$ test

Test insects: *Sitophilus granarius*

Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all of the test animals had been killed; 0% denotes that no test animals had been killed.

The active compounds, the concentrations of the active compounds and the results can be seen from the following table:

Table 9

(LD$_{100}$ test/*Sitophilus granarius*)

| Active compound | Active compound concentration of the solution in % | Degree of destruction in % |
|---|---|---|
| Compound (G) (known): O=P(S)(C$_2$H$_5$)(OC$_2$H$_5$)–O–[pyridazinone, NH] | 0.2<br>0.02 | 100<br>0 |

Table 9-continued (LD$_{100}$ test/*Sitophilus granarius*)

| Active compound | Active compound concentration of the solution in % | Degree of destruction in % |
|---|---|---|
| (known) (F) — O-P(OC$_2$H$_5$)$_2$, =O, pyridazinone N-phenyl | 0.2 / 0.02 | 100 / 0 |
| (known) (E) — O-P(OC$_2$H$_5$)$_2$, =S, N-CH$_2$-CH$_2$-CO-CH$_3$ | 0.2 / 0.02 | 100 / 0 |
| (known) (C) — O-P(OC$_2$H$_5$)$_2$, =S, N-CH$_2$-CO-OC$_2$H$_5$ | 0.2 / 0.02 | 100 / 0 |
| (14) — O-P(=S)(C$_2$H$_5$)(OCH$_3$), N-CH$_3$ | 0.2 | 100 |
| (15) — O-P(=S)(CH$_3$)(OC$_2$H$_5$), N-CH$_3$ | 0.02 | 100 |
| (1) — O-P(=S)(C$_2$H$_5$)(OC$_2$H$_5$), N-CH$_3$ | 0.02 | 100 |
| (16) — O-P(=S)(CH$_3$)(OC$_3$H$_7$-iso), N-CH$_3$ | 0.02 | 100 |
| (37) — O-P(=S)(C$_2$H$_5$)(OC$_2$H$_5$), 4-CH$_3$, N-CH$_3$ | 0.02 | 100 |
| (38) — O-P(=S)(C$_2$H$_5$)(OC$_3$H$_7$-n), 4-CH$_3$, N-CH$_3$ | 0.02 | 100 |
| (27) — O-P(=S)(CH$_3$)(OC$_2$H$_5$), 4-CH$_3$, N-CH$_3$ | 0.02 | 90 |
| (85) — O-P(=S)(CH$_3$)(OC$_3$H$_7$-iso), N-C$_3$H$_7$-iso | 0.02 | 100 |
| (81) — O-P(=S)(C$_2$H$_5$)(OC$_2$H$_5$), N-CH$_2$-CH=CH$_2$ | 0.02 | 100 |

Table 9-continued
(LD₁₀₀ test/*Sitophilus granarius*)

| Active compound | Active compound concentration of the solution in % | Degree of destruction in % |
|---|---|---|
| (95) Compound with S=P(OC₃H₇-n)(CH₃), O-linked to pyridazinone ring with N—CH₂—CH=CH₂ | 0.02 | 100 |
| (96) Compound with S=P(OC₃H₇-n)(CH₃), O-linked to pyridazinone ring with N—CH₂—C≡CH | 0.02 | 100 |
| (84) Compound with S=P(OC₂H₅)(C₂H₅), O-linked to pyridazinone ring with N—CH₂—C≡CH | 0.02 | 100 |
| (98) Compound with S=P(OC₃H₇-n)(CH₃), O-linked to pyridazinone ring with N—CH₂—CO—OC₂H₅ | 0.02 | 100 |
| (9) Compound with S=P(C₂H₅)(OC₃H₇-n), O-linked to pyridazinone ring with N—CH₂—CH₂—CO—O—CH₃ | 0.02 | 90 |
| (24) Compound with S=P(CH₃)(OC₂H₅), O-linked to pyridazinone ring with N—CH₂—CH₂—S—C₂H₅ | 0.02 | 100 |
| (25) Compound with S=P(CH₃)(OC₃H₇-iso), O-linked to pyridazinone ring with N—CH₂—CH₂—S—C₂H₅ | 0.02 | 100 |
| (56) Compound with S=P(C₂H₅)(OC₂H₅), O-linked to pyridazinone ring with N—CH₂—CH₂—Cl | 0.02 | 100 |
| (58) Compound with S=P(C₂H₅)(OCH₃), O-linked to pyridazinone ring with N—CH₂—CH₂—Cl | 0.02 | 100 |
| (20) Compound with S=P(C₂H₅)(OC₄H₉-iso), O-linked to pyridazinone ring with N—phenyl | 0.02 | 100 |
| (41) Compound with S=P(CH₃)(OC₂H₅), O-linked to pyridazinone ring with N—phenyl | 0.02 | 100 |
| (40) Compound with S=P(C₂H₅)(OC₃H₇-n), O-linked to pyridazinone ring with N—phenyl | 0.02 | 100 |

Table 9-continued
(LD$_{100}$ test/*Sitophilus granarius*)
| Active compound | Active compound concentration of the solution in % | Degree of destruction in % |
|---|---|---|
| (31) 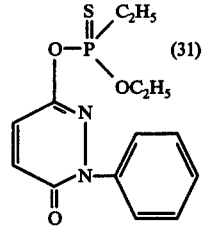 | 0.02 | 100 |
| (29) 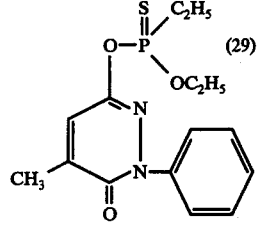 | 0.02 | 95 |
| (50) 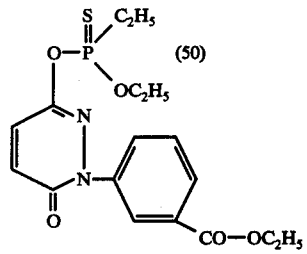 | 0.02 | 90 |
| (66) 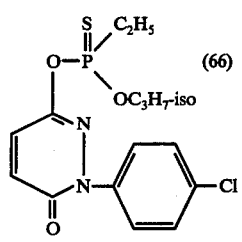 | 0.02 | 100 |
| (67) 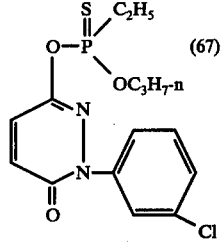 | 0.02 | 100 |
| (68) 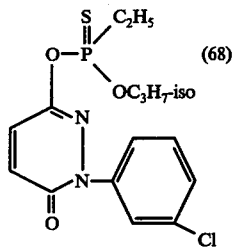 | 0.02 | 90 |
| (69) 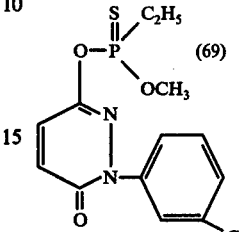 | 0.02 | 90 |
| (70) 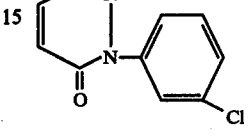 | 0.02 | 100 |
| (77) 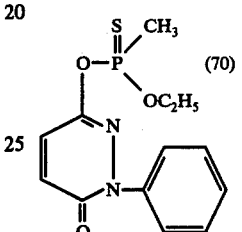 | 0.02 | 100 |
| (48) 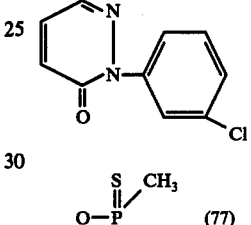 | 0.02 | 100 |
| (45) 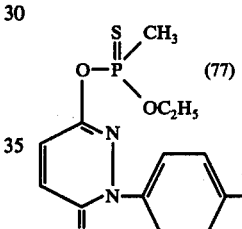 | 0.02 | 100 |
| (99) 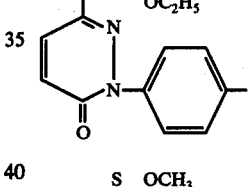 | 0.02 | 100 |

Table 9-continued (LD₁₀₀ test/*Sitophilus granarius*)

| Active compound | Active compound concentration of the solution in % | Degree of destruction in % |
|---|---|---|
| 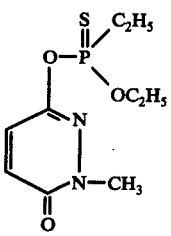 (43) | 0.02 | 100 |

The process of this invention is illustrated by the following preparative Examples.

EXAMPLE 10

(1)

26.1 g (0.15 mole) of O-ethyl-ethanethionophosphonic acid ester chloride were added dropwise to a suspension of 18.9 g (0.15 mole) of 3-hydroxy-1-methyl-6-pyridazinone and 21.4 g (0.155 mole) of potassium carbonate in 200 ml of acetonitrile. The mixture was warmed to 40° C for 3 hours, the solids were filtered off and the filtrate was poured into 200 ml of toluene. The toluene solution was washed with saturated sodium bicarbonate solution and water, dried over sodium sulfate and then concentrated. 24 g (61% of theory) of O-ethyl-O-[1-methyl-6-pyridazinon(3)yl]-thionoethane-phosphonic acid ester were obtained in the form of a brown oil of refractive index $n_D^{20}$: 1.5411.

The following compounds of the general formula

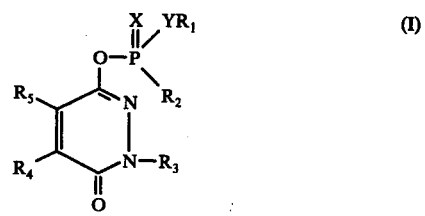

(I)

could be prepared analogously:

Table 10

| Compound No. | X | Y | R₁ | R₂ | R₃ | R₄ | R₅ | Yield (% of theory) | Physical data (refractive index: melting point, ° C) |
|---|---|---|---|---|---|---|---|---|---|
| 2 | S | O | —C₂H₅ | —C₂H₅ | —CH₂—CH₂—CO—CH₃ | H | H | 63 | $n_D^{22}$: 1.5396 |
| 3 | S | O | —C₂H₅ | —C₂H₅ | —CH₂—CH₂—CN | H | H | 57 | $n_D^{22}$: 1.5461 |
| 4 | S | O | —C₂H₅ | —CH₃ | —CH₂—CH₂—CN | H | H | 84 | 60 |
| 5 | S | O | —CH₃ | —C₂H₅ | —CH₂—CH₂—CN | H | H | 77 | $n_D^{24}$: 1.5474 |
| 6 | S | O | —C₃H₇-iso | —CH₃ | —CH₂—CH₂—CN | H | H | 86 | $n_D^{24}$: 1.5364 |
| 7 | S | O | —C₃H₇-n | —C₂H₅ | —CH₂—CH₂—CN | H | H | 83 | $n_D^{24}$: 1.5338 |
| 8 | S | O | —C₃H₇-n | —C₂H₅ | —CH₂—CH₂—CO—CH₃ | H | H | 61 | $n_D^{24}$: 1.5317 |
| 9 | S | O | —C₃H₇-n | —C₂H₅ | —CH₂—CH₂—CO—OCH₃ | H | H | 75 | $n_D^{24}$: 1.5228 |
| 10 | S | O | —C₂H₅ | —CH₃ | —CH₂—CH₂—CO—OCH₃ | H | H | 59 | $n_D^{24}$: 1.5320 |
| 11 | S | O | —C₂H₅ | —C₂H₅ | —CH₂—CH₂—CO—OCH₃ | H | H | 69 | $n_D^{24}$: 1.5318 |
| 12 | S | O | —C₂H₅ | —CH₃ | —CH₂—CH₂—CO—OC₂H₅ | H | H | 72 | $n_D^{24}$: 1.5240 |
| 13 | S | O | —C₂H₅ | —C₂H₅ | —CH₂—CH₂—CO—OC₂H₅ | H | H | 50 | $n_D^{25}$: 1.5253 |
| 14 | S | O | —CH₃ | —C₂H₅ | —CH₃ | H | H | 64 | $n_D^{22}$: 1.5506 |
| 15 | S | O | —C₂H₅ | —CH₃ | —CH₃ | H | H | 62 | 50 |
| 16 | S | O | —C₃H₇-iso | —CH₃ | —CH₃ | H | H | 66 | 60 |
| 17 | S | O | —CH₃ | —C₂H₅ | —CH₂—N(morpholino) | H | H | 58 | $n_D^{22}$: 1.5510 |
| 18 | S | O | —C₂H₅ | —CH₃ | —CH₂—N(piperidino) | H | H | 66 | $n_D^{22}$: 1.5420 |
| 19 | S | O | —C₂H₅ | —C₂H₅ | —CH₂—N(piperidino) | H | H | 55 | $n_D^{22}$: 1.5383 |
| 20 | S | O | —C₄H₉-iso | —C₂H₅ | —CH₂—N(phenyl) | H | H | 64 | partially crystalline |
| 21 | S | O | —C₂H₅ | —CH₃ | —CH₂—N(morpholino) | H | H | 53 | $n_D^{22}$: 1.5425 |

Table 10-continued

| Compound No. | X | Y | R₁ | R₂ | R₃ | R₄ | R₅ | Yield (% of theory) | Physical data (refractive index: melting point, °C) |
|---|---|---|---|---|---|---|---|---|---|
| 22 | S | O | —C₂H₅ | —C₂H₅ | —CH₂—N(morpholino) | H | H | 58 | $n_D^{22}$: 1.5412 |
| 23 | S | O | —C₃H₇-iso | —CH₃ | —CH₂—N(morpholino) | H | H | 55 | $n_D^{22}$: 1.5373 |
| 24 | S | O | —C₂H₅ | —CH₃ | —CH₂—CH₂—SC₂H₅ | H | H | 64 | $n_D^{22}$: 1.5421 |
| 25 | S | O | —C₃H₇-iso | —CH₃ | —CH₂—CH₂—SC₂H₅ | H | H | 51 | $n_D^{22}$: 1.5418 |
| 26 | S | O | —C₂H₅ | —C₂H₅ | —CH₂—CH₂—SC₂H₅ | H | H | 73 | $n_D^{22}$: 1.5406 |
| 27 | S | O | —C₂H₅ | —CH₃ | —CH₃ | H | CH₃ | 61 | 58 |
| 28 | S | O | —C₂H₅ | —C₂H₅ | —CH₂—C₆H₅ | H | CH₃ | 43 | 86 |
| 29 | S | O | —C₂H₅ | —C₂H₅ | —CH₂—C₆H₅ | CH₃ | H | 21 | $n_D^{26}$: 1.5702 |
| 30 | S | O | —CH₃ | —C₂H₅ | —CH₂—C₆H₅ | H | H | 65 | 67 |
| 31 | S | O | —C₂H₅ | —C₂H₅ | —CH₂—C₆H₅ | H | H | 71 | 57 |
| 32 | S | O | —C₃H₇-iso | —CH₃ | —CH₂—C₆H₅ | H | H | 68 | 62 |
| 33 | S | O | —C₃H₇-iso | —C₂H₅ | —CH₂—C₆H₅ | H | H | 62 | 75 |
| 34 | S | O | —CH₃ | —C₂H₅ | —CH₃ | H | CH₃ | 66 | 63 |
| 35 | S | O | —CH₃ | —C₂H₅ | —CH₃ | CH₃ | H | 11 | $n_D^{20}$: 1.5357 |
| 36 | S | O | —C₃H₇-iso | —C₂H₅ | —CH₃ | H | CH₃ | 62 | 79 |
| 37 | S | O | —C₂H₅ | —C₂H₅ | —CH₃ | H | CH₃ | 65 | $n_D^{20}$: 1.5000 |
| 38 | S | O | —C₃H₇-n | —C₂H₅ | —CH₃ | H | CH₃ | 76 | $n_D^{22}$: 1.5350 |
| 39 | S | O | —CH₃ | —CH₃ | —CH₂—C₆H₅ | H | H | 37 | 70 |
| 40 | S | O | —C₃H₇-n | —C₂H₅ | —CH₂—C₆H₅ | H | H | 65 | 48 |
| 41 | S | O | —C₂H₅ | —CH₃ | —CH₂—C₆H₅ | H | H | 65 | 67 |
| 42 | S | O | —C₃H₇-iso | —CH₃ | —CH₂—C₆H₄—CH₃ | H | H | 75 | $n_D^{22}$: 1.5632 |
| 43 | S | O | —C₂H₅ | —C₂H₅ | —CH₂—C₆H₄—Cl | H | H | 65 | $n_D^{22}$: 1.5703 |
| 44 | S | O | —C₃H₇-iso | —CH₃ | —CH₂—C₆H₄—Cl | H | H | 63 | $n_D^{22}$: 1.5667 |
| 45 | S | O | —CH₃ | —C₂H₅ | —CH₂—C₆H₄—Cl | H | H | 42 | 62 |

Table 10-continued

| Compound No. | X | Y | R₁ | R₂ | R₃ | R₄ | R₅ | Yield (% of theory) | Physical data (refractive index: melting point, °C) |
|---|---|---|---|---|---|---|---|---|---|
| 46 | S | O | $-C_3H_7$-n | $-C_2H_5$ | $-CH_2-C_6H_4-Cl$ (p) | H | H | 60 | $n_D^{19}$: 1.5632 |
| 47 | S | O | $-C_2H_5$ | $-C_2H_5$ | $-CH_2-C_6H_4-CH_3$ (p) | H | H | 80 | $n_D^{19}$: 1.5695 |
| 48 | S | O | $-CH_3$ | $-C_2H_5$ | $-CH_2-C_6H_4-CH_3$ (p) | H | H | 68 | $n_D^{21}$: 1.5770 |
| 49 | S | O | $-C_3H_7$-iso | $-C_2H_5$ | $-CH_2-C_6H_4-Cl$ (p) | H | H | 68 | $n_D^{21}$: 1.5673 |
| 50 | S | O | $-C_2H_5$ | $-C_2H_5$ | $-C_6H_4-CO-OC_2H_5$ (m) | H | H | 71 | $n_D^{19}$: 1.5662 |
| 51 | S | O | $-C_3H_7$-iso | $-CH_3$ | $-C_6H_4-CO-OC_2H_5$ (m) | H | H | 68 | $n_D^{19}$: 1.5645 |
| 52 | S | O | $-CH_3$ | $-C_2H_5$ | $-C_6H_4-CO-OC_2H_5$ (m) | H | H | 66 | 73 |
| 53 | S | O | $-C_2H_5$ | $-C_2H_5$ | $-CH_2-CH_2OH$ | H | H | 63 | $n_D^{21}$: 1.5368 |
| 54 | S | O | $-C_3$ | $-C_2H_5$ | $-CH_2-CH_2OH$ | H | H | 52 | $n_D^{20}$: 1.5512 |
| 55 | S | O | $-C_3H_7$-iso | $-CH_3$ | $-CH_2-CH_2OH$ | H | H | 57 | $n_D^{20}$: 1.5326 |
| 56 | S | O | $-C_2H_5$ | $-C_2H_5$ | $-CH_2-CH_2Cl$ | H | H | 74 | $n_D^{20}$: 1.5448 |
| 57 | S | O | $-C_3H_7$-iso | $-CH_3$ | $-CH_2-CH_2Cl$ | H | H | 74 | $n_D^{20}$: 1.5390 |
| 58 | S | O | $-CH_3$ | $-C_2H_5$ | $-CH_2-CH_2Cl$ | H | H | 13 | $n_D^{20}$: 1.5645 |
| 59 | S | S | $-C_4H_9$-sec. | $-CH_3$ | $-CH_3$ | H | H | 55 | $n_D^{22}$: 1.5360 |
| 60 | S | S | $-C_4H_9$-sec. | $-CH_3$ | $-C_6H_4-CH_3$ (p) | H | H | 68 | $n_D^{22}$: 1.5450 |
| 61 | S | S | $-C_4H_9$-sec. | $-CH_3$ | $-C_6H_5$ | H | H | 36 | 85–95 |
| 62 | S | S | $-C_4H_9$-sec. | $-CH_3$ | $-C_6H_4-Cl$ (p) | H | H | 65 | $n_D^{22}$: 1.5330 |
| 63 | S | S | $-C_4H_9$-sec. | $-CH_3$ | $-C_6H_4-NO_2$ (p) | H | H | 42 | $n_D^{21}$: 1.5510 |
| 64 | S | O | $-C_2H_5$ | $-CH_3$ | $-C_6H_4-Cl$ (p) | H | H | 40 | 90 |
| 65 | S | O | $-C_3H_7$-iso | $-CH_3$ | $-C_6H_4-Cl$ (p) | H | H | 62 | 75 |

Table 10-continued

| Compound No. | X | Y | $R_1$ | $R_2$ | $R_3$ | $R_4$ | $R_5$ | Yield (% of theory) | Physical data (refractive index: melting point, °C) |
|---|---|---|---|---|---|---|---|---|---|
| 66 | S | O | —C₃H₇-iso | —C₂H₅ | —C₆H₄-Cl (p) | H | H | 60 | $n_D^{24}$: 1.5762 |
| 67 | S | O | —C₃H₇-n | —C₂H₅ | —C₆H₄-Cl (m) | H | H | 65 | $n_D^{24}$: 1.5761 |
| 68 | S | O | —C₃H₇-iso | —C₂H₅ | —C₆H₄-Cl (m) | H | H | 64 | $n_D^{24}$: 1.5728 |
| 69 | S | O | —CH₃ | —C₂H₅ | —C₆H₄-Cl (m) | H | H | 32 | 76–78 |
| 70 | S | O | —C₂H₅ | —CH₃ | —C₆H₄-Cl (m) | H | H | 32 | $n_D^{24}$: 1.6060 |
| 71 | S | O | —C₃H₇-iso | —CH₃ | —C₆H₄-CH₃ (p) | H | H | 61 | $n_D^{24}$: 1.5740 |
| 72 | S | O | —CH₃ | —C₂H₅ | —C₆H₄-CH₃ (p) | H | H | 50 | $n_D^{24}$: 1.5921 |
| 73 | S | O | —C₃H₇-n | —C₂H₅ | —C₆H₄-CH₃ (p) | H | H | 66 | $n_D^{24}$: 1.5668 |
| 74 | S | O | —C₃H₇-iso | —C₂H₅ | —C₆H₄-CH₃ (p) | H | H | 64 | $n_D^{24}$: 1.5603 |
| 75 | S | O | —C₃H₇-iso | —C₂H₅ | —C₆H₄-NO₂ (p) | H | H | 22 | 63 |
| 76 | S | O | —C₃H₇-n | —C₂H₅ | —C₆H₄-NO₂ (p) | H | H | 23 | $n_D^{24}$: 1.5710 |
| 77 | S | O | —C₂H₅ | —CH₃ | —C₆H₄-CH₃ (p) | H | H | 56 | $n_D^{24}$: 1.5883 |
| 78 | S | O | —C₄H₉-iso | —C₂H₅ | —CH₃ | H | H | 86 | $n_D^{25}$: 1.5231 |
| 79 | S | O | —C₄H₉-iso | —C₂H₅ | —CH₂—N(morpholino) | H | H | 81 | $n_D^{25}$: 1.5305 |
| 80 | S | O | —C₄H₉-sec. | —CH₃ | —CH₃ | H | H | 81 | $n_D^{23}$: 1.5328 |

EXAMPLE 11

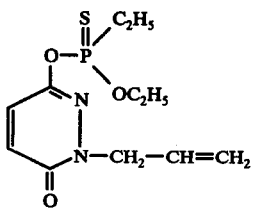
(81)

12.1 g (0.1 mole) of allyl bromide were added dropwise at 20° C to a suspension of 24.8 g (0.1 mole) of O-ethyl-O-[1,6-dihydro-6-pyridazinon(3)yl]-ethanethionophosphonic acid ester and 11.2 g (0.1 mole) of potassium tert.-butylate in 200 ml of acetonitrile. The mixture was allowed to continue reacting for 3 hours at 60° C and was then cooled, and the batch was poured into 200 ml of toluene. The toluene solution was washed with water, dried over sodium sulfate and then evaporated. 21 g (73% of theory) of O-ethyl-O-[1-allyl-6-pyridazinon(3)yl]-thionoethanephosphonic acid ester were obtained in the form of a brown oil of refractive index $n_D^{22}$: 1.5309.

The following compounds of the general formula (VIII)

were prepared analogously:

Table 11

| Compound No. | X | Y | R₁ | R₂ | R₃ | Yield (% of theory) | Physical data (refractive index; melting point ° C) |
|---|---|---|---|---|---|---|---|
| 82 | S | O | —C₂H₅ | —C₂H₅ | —CH₂—CO—OC₂H₅ | 68 | 54 |
| 83 | S | O | —C₂H₅ | —C₂H₅ | —CH₂—CN | 56 | $n_D^{20}$:1.5476 |
| 84 | S | O | —C₂H₅ | —C₂H₅ | —CH₂—C≡CH | 56 | $n_D^{20}$:1.5392 |
| 85 | S | O | —C₃H₇-iso | —CH₃ | —C₃H₇-iso | 48 | $n_D^{20}$:1.5240 |
| 86 | S | O | —C₃H₇-iso | —CH₃ | —CH₂—C≡CH | 80 | $n_D^{20}$:1.5380 |
| 87 | S | O | —C₃H₇-iso | —CH₃ | —CH₂—CO—OC₂H₅ | 81 | 51 |
| 88 | S | O | —C₃H₇-iso | —CH₃ | —CH₂—CH=CH₂ | 73 | $n_D^{23}$:1.5391 |
| 89 | S | O | —C₃H₇-iso | —CH₃ | —CH₂—CN | 84 | $n_D^{23}$:1.5324 |

EXAMPLE 12

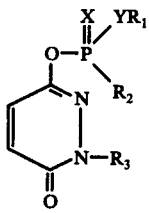
(90)

A mixture of 24.8 g (0.1 mole) of O-ethyl-O-[1,6-dihydro-6-pyridazinon(3)yl]-ethanethionophosphonic acid ester and 50 ml of a 30% strength formalin solution was heated to 100° C for 10 minutes. The batch was then cooled and extracted with methylene chloride, and the organic phase was dried over sodium sulfate and concentrated. 23 g (84% of theory) of O-ethyl-O-[1-hydroxymethyl-6-pyridazinon(3)yl]-thionoethanephosphonic acid ester were obtained in the form of a yellow oil of refractive index $n_D^{22}$: 1.5405.

The following compound (91)

was synthesized analogously; yield 84% of theory, m.p. 139° C.

EXAMPLE 13

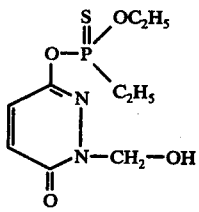
(92)

A mixture of 24.8 g (0.1 mole) of O-ethyl-O-[1,6-dihydro-6-pyridazinon(3)yl]-ethanethionophosphonic acid ester and 50 ml of 30% strength formalin solution was heated to 100° C for 10 minutes, then cooled, and extracted twice with a total of 200 ml of carbon tetrachloride. 13.5 g (0.1 mole) of thionyl chloride were added dropwise to the carbon tetrachloride solution. The mixture was then warmed to 70° C for 2 hours, cooled, washed with saturated sodium bicarbonate solution and water and dried over sodium sulfate. After stripping off the solvent, 22 g (74% of theory) of O-ethyl-O-[1-chloromethyl-6-pyridazinon(3)yl]-thionoethanephosphonic acid ester were obtained in the form of a yellow oil of refractive index $n_D^{19}$: 1.5426.

The following compound

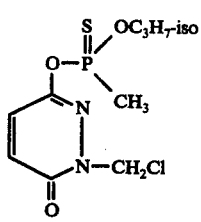
(93)

were synthesised analogously, yield 62% of theory, m.p. 61° C.

Other compounds which can be similarly prepared include:

Table 12

| Compound No. | X | Y | R₁ | R₂ | R₃ | R₄ | R₅ |
|---|---|---|---|---|---|---|---|
| 100 | O | O | —C₂H₅ | —C₂H₅ | NO₂-C₆H₃(-COOC₃H₇-iso)- | H | H |
| 101 | O | O | —C₂H₅ | —C₂H₅ | —CH₂-C₆H₃(Cl)(CH₃) | H | H | and the like.

It will be appreciated that the instant specification and examples are set forth by way of illustration and not limitation, and that various modifications and changes may be made without departing from the spirit and scope of the present invention.

What we claim is:

1. An O-[1-substituted-6-pyridazinon(3)yl](thiono)(-thiol)-alkanephosphonic acid ester of the formula

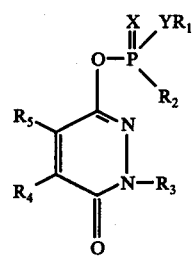

in which
R₁ and R₂ each independently is alkyl with 1 to 7 carbon atoms,
R₃ is alkyl, cyanoalkyl, alkylcarbonylalkyl, carbalkoxyalkyl, hydroxyalkyl, alkylthioalkyl or halogenoalkyl with 1 to 4 carbon atoms per alkyl radical, alkenyl or alkenyl with 3 to 5 carbon atoms, benzyl, benzyl carrying at least one substituent selected from halogen and alkyl with 1 to 3 carbon atoms, or phenyl, phenyl carrying at least one substituent selected from nitro, halogen, alkyl with 1 to 3 carbon atoms and carbalkoxy with 1 to 4 carbon atoms, or piperidinomethyl,
R₄ and R₅ each independently is hydrogen or alkyl with 1 to 3 carbon atoms, and
X and Y each independently is oxygen or sulfur.

2. An ester according to claim 1, in which X is sulfur, Y is oxygen, R₁ is alkyl with 1 to 5 carbon atoms, R₂ is alkyl with 1 to 3 carbon atoms, R₄ and R₅ each independently is hydrogen or methyl, and R₃ is alkenyl or alkynyl with 3 or 4 carbon atoms, hydroxyalkyl, cyanoalkyl, alkylthioalkyl, chloroalkyl, methylcarbonylalkyl, ethylcarbonylalkyl, carbalkoxyalkyl or alkyl, each with 1 to 3 carbon atoms per alkyl radical, benzyl chlorobenzyl, methylbenzyl, phenyl, phenyl substituted by nitro, chlorine, methyl, ethyl or carbalkoxy with 1 to 3 carbon atoms in the alkoxy radical, or piperidinomethyl.

3. An ester according to claim 1 wherein such ester is O-methyl-O-[1-methyl-6-pyridazinon(3)yl]-thionoethanephosphonic acid of the formula

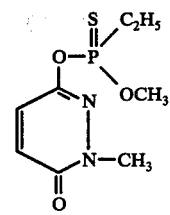

4. An ester according to claim 1 wherein such ester is O-ethyl-O-[1-phenyl-6-pyridazinon(3)yl]-thionoethanephosphonic acid ester of the formula

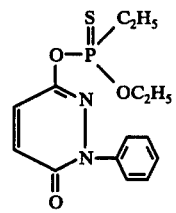

5. An ester according to claim 1 wherein such ester is O-n-propyl-O-[1-phenyl-6-pyridazinon(3)yl]-thionoethanephosphonic acid ester of the formula

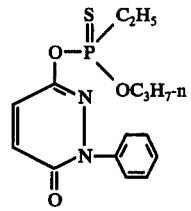

6. An ester according to claim 1 wherein such ester is O-ethyl-O-[1-β-chloroethyl-6-pyridazinon(3)yl]-thionoethanephosphonic acid ester of the formula

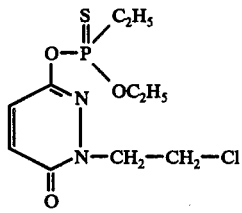

7. An ester according to claim 1 wherein such ester is O-ethyl-O-[1-allyl-6-pyridazinon(3)yl]-thionoethanephosphonic acid ester of the formula

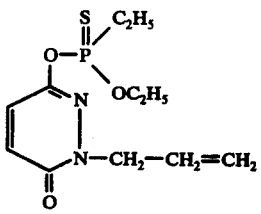

8. An insecticidal or acaricidal composition containing as active ingredient an insecticidally or acaricidally effective amount of an ester according to claim 1 and a carrier.

9. A method of combating insects or acarids which comprises applying to the insects or acarids or to a habitat thereof an insecticidally or acaricidally effective amount of an ester according to claim 1.

10. The method according to claim 9 in which said ester is
O-methyl-O-[1-methyl-6-pyridazinon(3)yl]-thionoethanephosphonic acid,
O-ethyl-O-[1-phenyl-6-pyridazinon(3)yl]-thionoethanephosphonic acid ester,
O-n-propyl-O-[1-phenyl-6-pyridazinon(3)yl]-thionoethanephosphonic acid ester,
O-ethyl-O-[1-β-chloroethyl-6-pyridazinon(3)yl]thionoethanephosphonic acid ester, or
O-ethyl-O-[1-allyl-6-pyridazinon(3)yl]-thionoethanephosphonic acid ester.